(12) United States Patent
Steiner et al.

(10) Patent No.: US 6,221,107 B1
(45) Date of Patent: Apr. 24, 2001

(54) LIGAMENT FIXATION DEVICE AND METHOD

(75) Inventors: Mark E. Steiner, 7 Hewins Farm Rd, Wellesley, MA (US) 02481; Dennis W. Burke; John Prudden, Jr., both of Milton, MA (US)

(73) Assignee: Mark E. Steiner, Wellsely, MA (US)

( * ) Notice: Subject to any disclaimer, the term of this patent is extended or adjusted under 35 U.S.C. 154(b) by 0 days.

(21) Appl. No.: 09/128,145

(22) Filed: Aug. 3, 1998

(51) Int. Cl.[7] ........................................ A61F 2/08
(52) U.S. Cl. ................... 623/13.14; 623/13.13; 623/13.19
(58) Field of Search ............... 623/13, 13.11–13.2

(56) References Cited

U.S. PATENT DOCUMENTS

| Re. 13,204 | 2/1911 | Jossart . | |
|---|---|---|---|
| Re. 34,871 | 3/1995 | McGuire et al. | 606/73 |
| 2,353,851 | 7/1944 | Rosan | 85/2.4 |
| 3,153,975 | 10/1964 | Rapata | 85/80 |
| 3,199,398 | 8/1965 | Weisz | 85/83 |
| 3,411,397 | 11/1968 | Birmingham | 85/72 |
| 3,516,324 | 6/1970 | Berner | 85/83 |
| 3,678,798 | 7/1972 | Van Niel | 85/81 |
| 3,765,295 | 10/1973 | Ptak | 85/72 |
| 3,832,931 | 9/1974 | Talan | 85/83 |
| 3,953,896 | 5/1976 | Treace | 3/1 |
| 3,976,079 | 8/1976 | Samuels et al. | 128/335 |
| 3,988,783 | 11/1976 | Treace | 3/1 |
| 4,011,602 | 3/1977 | Rybicki et al. | 3/1.9 |
| 4,083,289 | 4/1978 | Erickson | 85/72 |
| 4,085,651 | 4/1978 | Koscik | 85/72 |

(List continued on next page.)

FOREIGN PATENT DOCUMENTS

| 1015989 | 8/1977 | (CA) . | |
|---|---|---|---|
| 3710587 | * 10/1988 | (DE) | 623/13 |
| 0 052 573 | 5/1982 | (EP) . | |
| 0 278 713 | 8/1988 | (EP) . | |
| 0 330 328 | 8/1989 | (EP) . | |
| 0 358 372 | 3/1990 | (EP) . | |
| 0 596 177 | 5/1994 | (EP) . | |
| 2 590 792 | 5/1987 | (FR) . | |
| 2 586 927 | 11/1987 | (FR) . | |
| 2 622 430 | 5/1989 | (FR) . | |
| 2636835 | * 3/1990 | (FR) | 623/13 |
| 1082415 | 3/1984 | (RU) . | |

OTHER PUBLICATIONS

Beck et al., "Anterior Cruciate Ligament Reconstruction With The Endoscopic Technique"; *Operative Techniques in Orthopaedics*, vol. 2, No. 2, pp. 86–98 (1992).

Steiner et al., "Anterior Cruciate Ligament Graft Fixation; Comparison of Hamstring and Patellar Tendon Grafts", *The American Journal of Sports Medicine*; vol. 22, No. 2; (1994).

*Primary Examiner*—Michael J. Milano
(74) *Attorney, Agent, or Firm*—Fish & Richardson P.C.

(57) ABSTRACT

The invention relates to a device for attaching a ligament graft to the inside of a bone passage from a proximal location, the device including (1) a non-expansible ring having an interior passage through which the ligament graft may extend, the ring sized to fit within the bone passage; (2) a radially expansible gripping member sized to enter the ring and to press the ligament outwardly against the interior surface of the ring; and (3) an expander coupled to the expansible gripping member, constructed to expand the expansible gripping member to grip the ligament against the ring.

25 Claims, 11 Drawing Sheets

U.S. PATENT DOCUMENTS

| | | | |
|---|---|---|---|
| 4,301,551 | 11/1981 | Dore et al. | 3/1 |
| 4,407,618 | 10/1983 | Kimura | 411/40 |
| 4,464,076 | 8/1984 | Leibhard | 403/297 |
| 4,520,511 | 6/1985 | Gianezio et al. | 3/1.913 |
| 4,535,925 | 8/1985 | Ramey et al. | 227/55 |
| 4,580,936 | 4/1986 | Francis et al. | 411/38 |
| 4,590,928 | 5/1986 | Hunt et al. | 128/92 D |
| 4,632,100 | 12/1986 | Somers et al. | 128/92 |
| 4,662,886 | 5/1987 | Moorse et al. | 623/13 |
| 4,693,248 | 9/1987 | Failla | 128/334 |
| 4,711,232 | 12/1987 | Fischer et al. | 128/92 YF |
| 4,711,234 | 12/1987 | Vives et al. | 128/92 YF |
| 4,716,892 | 1/1988 | Fischer et al. | 128/92 YF |
| 4,738,255 | 4/1988 | Goble et al. | 128/92 YF |
| 4,741,330 | 5/1988 | Hayhurst | 128/92 YF |
| 4,744,793 | 5/1988 | Parr et al. | 623/13 |
| 4,755,183 | 7/1988 | Kenna | 623/13 |
| 4,772,286 * | 9/1988 | Goble | 623/13 |
| 4,776,329 | 10/1988 | Treharne | 128/92 YF |
| 4,778,468 | 10/1988 | Hunt et al. | 623/16 |
| 4,784,126 | 11/1988 | Hourahane | 128/92 YF |
| 4,790,850 | 12/1988 | Dunn et al. | 623/13 |
| 4,828,562 | 5/1989 | Kenna | 623/13 |
| 4,834,752 | 5/1989 | Van Kampen | 623/13 |
| 4,851,005 | 7/1989 | Hunt et al. | 623/18 |
| 4,863,476 | 9/1989 | Shepperd | 623/17 |
| 4,870,957 | 10/1989 | Goble et al. | 128/92 YF |
| 4,888,022 | 12/1989 | Huebsch | 623/22 |
| 4,895,150 | 1/1990 | Isaacson et al. | 128/419 R |
| 4,927,421 | 5/1990 | Goble et al. | 606/73 |
| 4,940,467 | 7/1990 | Tronzo | 606/66 |
| 4,944,742 | 7/1990 | Clemow et al. | 606/59 |
| 4,950,270 | 8/1990 | Bowman et al. | 606/72 |
| 4,950,271 | 8/1990 | Lewis et al. | 606/102 |
| 4,955,910 | 9/1990 | Bolesky | 623/13 |
| 4,960,420 | 10/1990 | Goble et al. | 606/72 |
| 4,997,433 * | 3/1991 | Goble | 623/13 |
| 5,002,574 * | 3/1991 | May | 623/13 |
| 5,013,316 | 5/1991 | Goble et al. | 606/72 |
| 5,037,422 | 8/1991 | Hayhurst et al. | 606/72 |
| 5,062,843 | 11/1991 | Mahony, III | 606/53 |
| 5,108,431 | 4/1992 | Mansat et al. | 623/13 |
| 5,108,433 | 4/1992 | May et al. | 623/13 |
| 5,129,902 | 7/1992 | Goble et al. | 606/65 |
| 5,147,362 | 9/1992 | Goble | 606/72 |
| 5,151,104 * | 9/1992 | Kenna | 623/13 |
| 5,152,790 | 10/1992 | Rosenberg et al. | 623/13 |
| 5,176,682 | 1/1993 | Chow | 606/72 |
| 5,211,647 | 5/1993 | Schmieding | 606/104 |
| 5,234,430 | 8/1993 | Huebner | 606/60 |
| 5,236,445 | 8/1993 | Hayhurst et al. | 606/232 |
| 5,258,016 | 11/1993 | DiPoto et al. | 606/232 |
| 5,268,001 | 12/1993 | Nicholson et al. | 606/72 |
| 5,282,802 | 2/1994 | Mahony, III | 606/72 |
| 5,312,438 | 5/1994 | Johnson | 606/232 |
| 5,324,308 | 6/1994 | Pierce | 606/232 |
| 5,356,435 * | 10/1994 | Thein | 623/13 |
| 5,360,448 | 11/1994 | Thramann | 623/16 |
| 5,372,599 | 12/1994 | Martins | 606/75 |
| 5,376,119 | 12/1994 | Zimmermann et al. | 673/13 |
| 5,383,878 | 1/1995 | Roger et al. | 606/73 |
| 5,383,905 | 1/1995 | Golds et al. | 606/232 |
| 5,423,819 | 6/1995 | Small et al. | 606/73 |
| 5,425,707 | 6/1995 | Goldberg | 604/51 |
| 5,425,767 | 6/1995 | Steininger et al. | 623/13 |
| 5,531,792 | 7/1996 | Huene | 623/16 |
| 5,571,184 | 11/1996 | DeSatnick | 623/11 |
| 5,632,748 | 5/1997 | Beck, Jr. et al. | 606/89 |
| 5,643,266 | 7/1997 | Li | 606/72 |
| 5,645,589 | 7/1997 | Li | 623/16 |
| 5,690,649 | 11/1997 | Li | 606/139 |
| 5,702,215 | 12/1997 | Li | 411/21 |
| 5,702,397 | 12/1997 | Goble et al. | 606/72 |
| 5,702,398 | 12/1997 | Tarabishy | 606/72 |
| 5,707,395 | 1/1998 | Li | 606/232 |
| 5,766,250 * | 6/1998 | Chervitz | 623/13 |
| 5,899,938 * | 5/1999 | Sklar | 623/13 |
| 5,961,520 | 10/1999 | Beck, Jr. et al. | 606/72 |

* cited by examiner

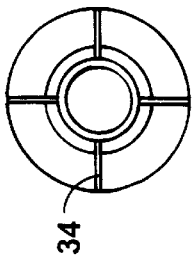
FIG. 1A
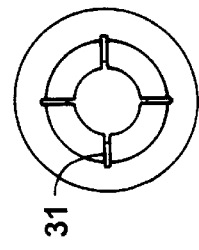
FIG. 1B
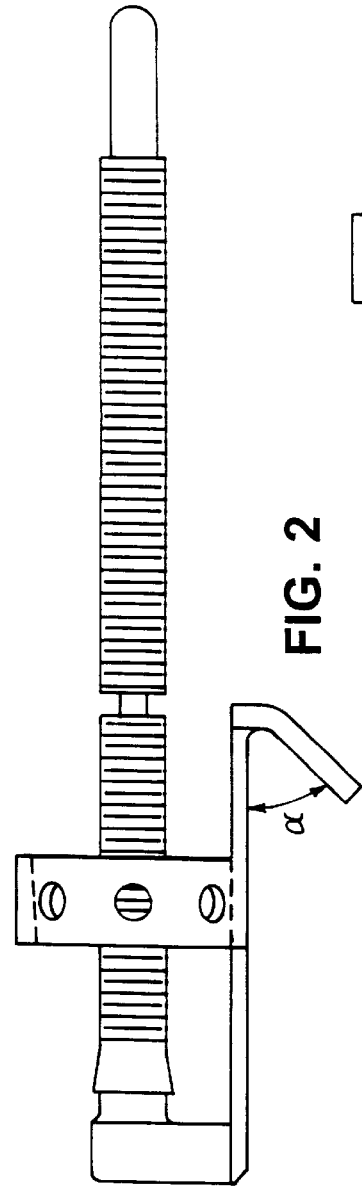
FIG. 2
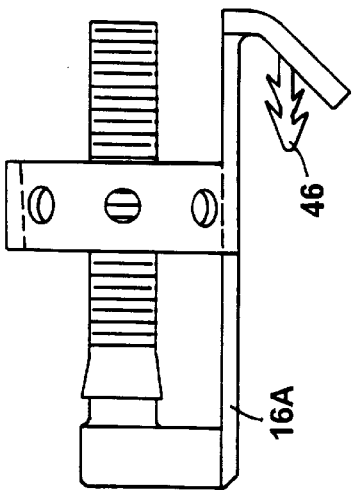
FIG. 2A
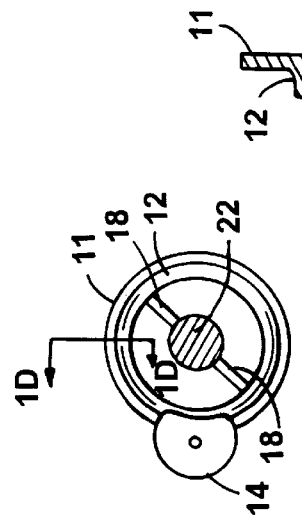
FIG. 1C
FIG. 1D

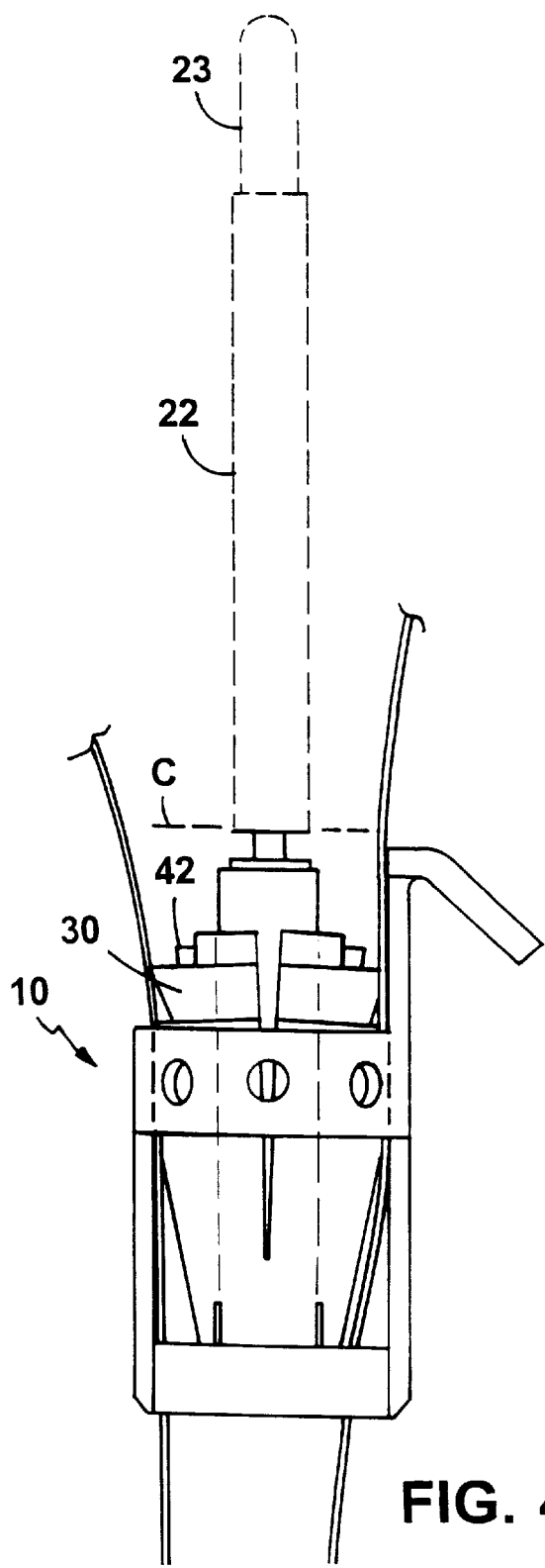
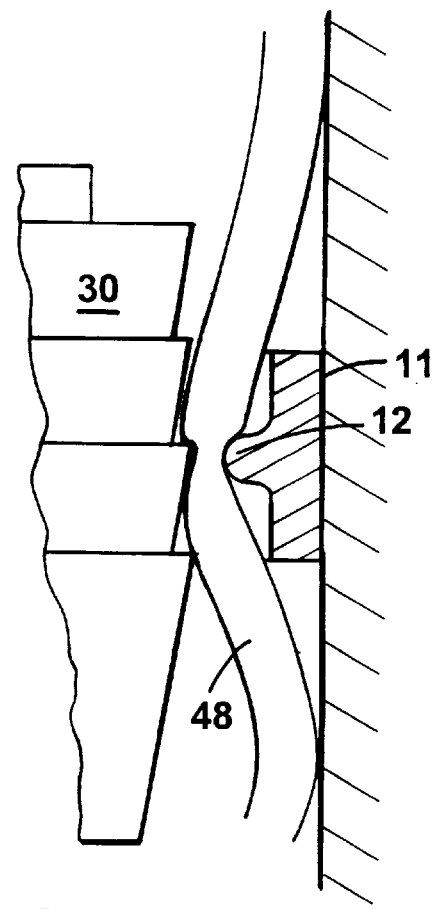
FIG. 4
FIG. 4A

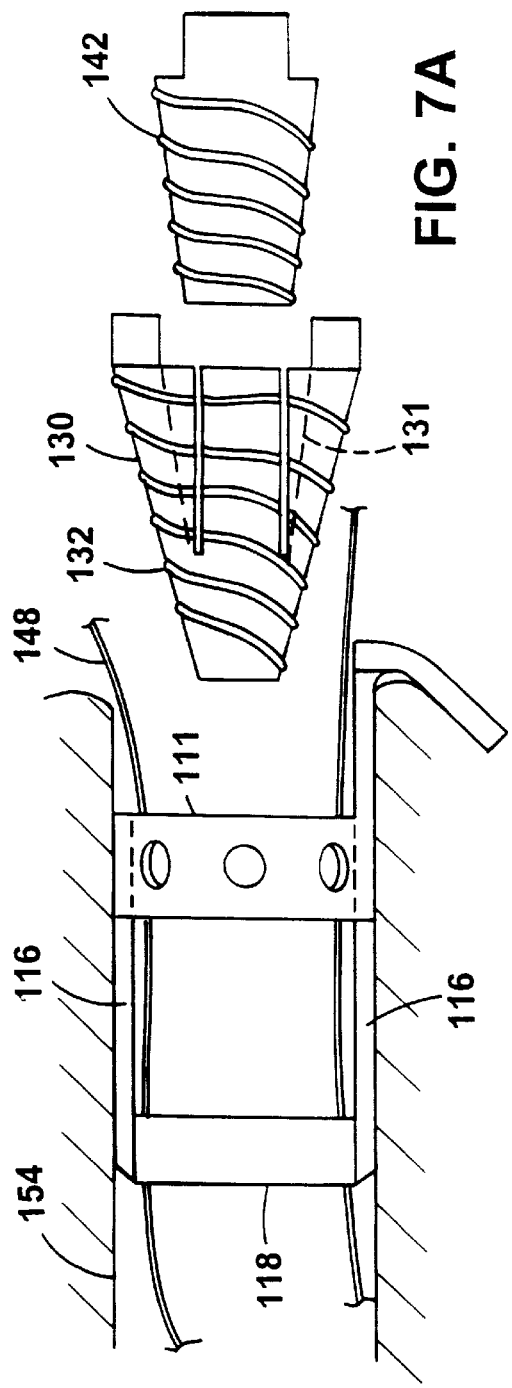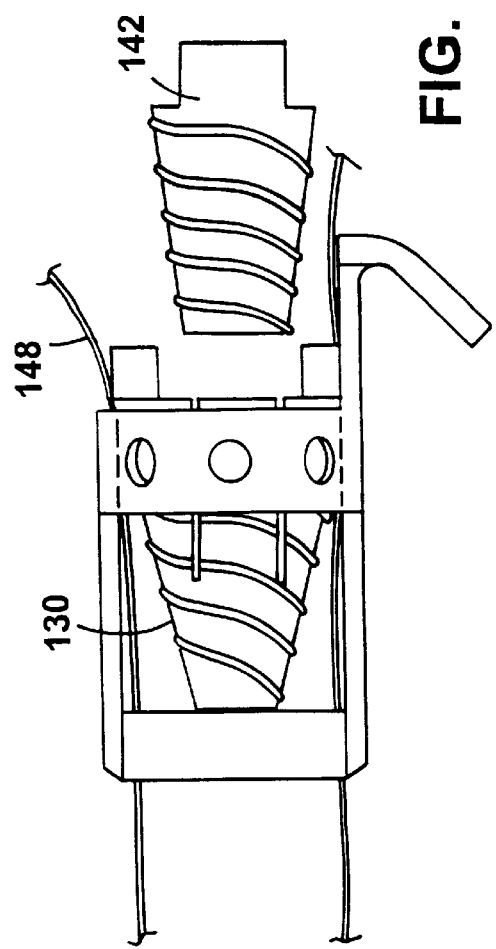
FIG. 7A
FIG. 7B

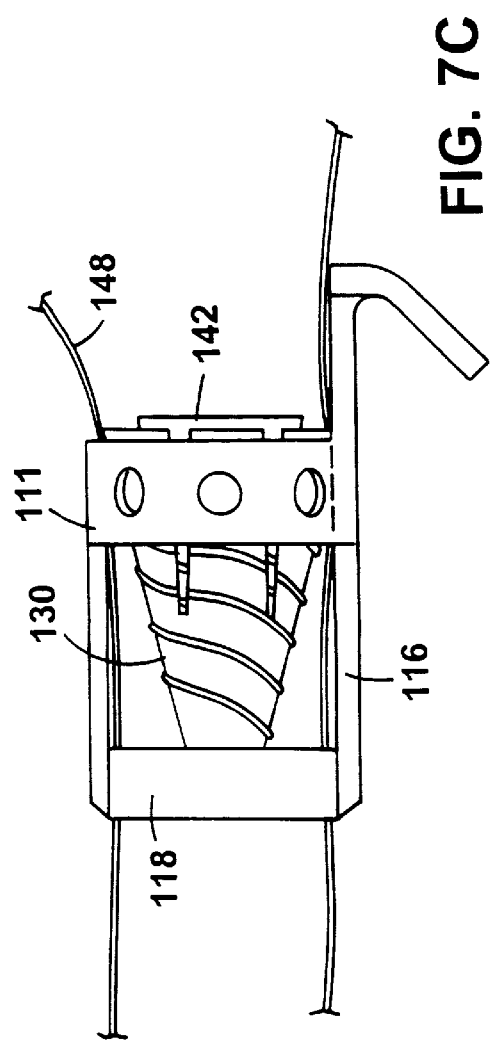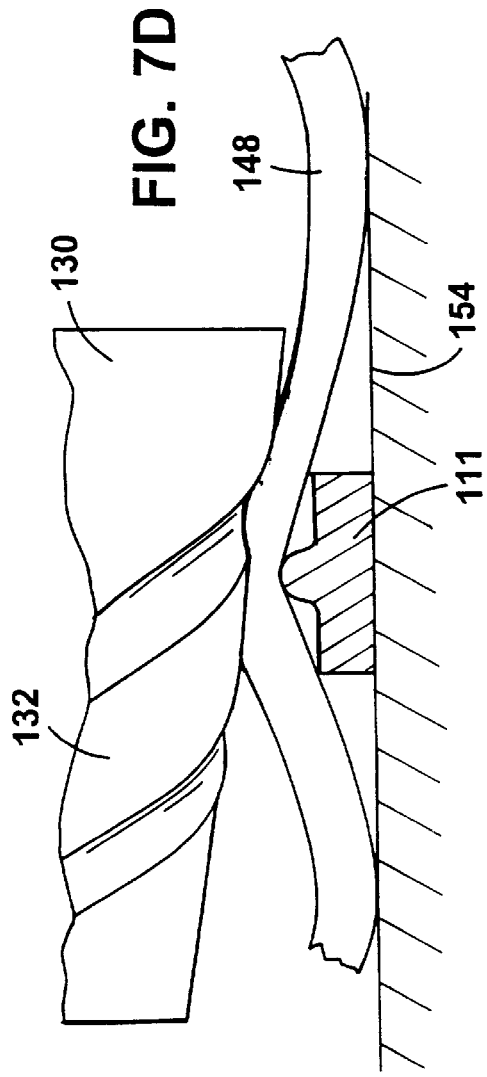

LIGAMENT FIXATION DEVICE AND METHOD

BACKGROUND OF THE INVENTION

This invention relates to fixation of ligament grafts.

When a ligament ruptures, it is usually replaced by a ligament graft or a prosthetic ligament. In many cases, a ligament graft is preferable because prosthetic ligaments can wear out.

For example, the anterior cruciate ligament (ACL) when ruptured, often requires replacement and a graft is preferred.

In such ACL reconstruction procedures, a bone tunnel is created through the tibia and one through the femur. The ligament graft is then affixed to each bone tunnel by a variety of means, with the goal that the graft will securely heal to the bone in the tunnel.

Presently available techniques are not satisfactory in all respects.

SUMMARY OF THE INVENTION

According to one aspect of the invention a device is provided for attaching a ligament graft to the inside of a bone tunnel from its proximal aspect (extra-articular point of access). The device comprises: a non-expansible ring having an-interior passage through which the ligament graft may extend, the ring sized and adapted to fit within and be secured in the bone tunnel; a radially expansible gripping member sized to enter the ring and to press the ligament outwardly against the interior surface of the ring; and an expander coupled to the expansible gripping member, constructed to expand the expansible gripping member to grip and secure the ligament against the ring.

Preferred embodiments of this aspect of the invention have one or more of the following features.

The gripping member, when in position within the ring, has a distal portion extending beyond the ring that positions a corresponding portion of the ligament near or against the surface of the bone tunnel, in the path of in-growing bone.

The ring is rigid.

The ring includes at least one aperture disposed to permit in-growth of bone through the side of the ring and about the ligament graft.

The device further comprises at least one strut extending distally from the ring and a distal member is disposed at the distal end of the strut in position to limit distal movement of the gripping member. Preferably there are one strut or two spaced apart struts that extend distally, in supporting relationship with said distal member. Preferably the distal member is a base from which a threaded rod extends proximally through the ring passage, the gripping member being expanded by a threaded expander engaged upon the threaded rod, preferably the threaded expander being of wedge form, arranged to radially wedge apart portions of the expansible gripping member.

Preferably, in the foregoing case or generally, a strut extends proximally from the ring to a securing member attached to its proximal end, the securing member being constructed and arranged to engage an exterior surface of the bone to secure the ring in the cortical region of the bone passage.

The expansible gripping member comprises a set of circumferentially arranged proximally extending leg portions constructed and arranged to be splayed apart by the wedging action of a centrally introduced expander member, preferably the exterior surface of the gripping member leg portions have ligament gripping projections. In certain preferred embodiments the gripping projections comprise portions of at least one barb or ledge and preferably an axially spaced set of, circumferential ledge or barb and in other preferred embodiments the gripping projection comprise screw threads, including lands, preferably of helical form.

The ring supports a threaded rod that extends through the gripping member, in combination with a threaded expander wedge member constructed and arranged to be threaded on the threaded rod into the expansible gripping member in a wedging relationship.

The expansible gripping member supports a threaded rod extending proximally from the gripping member in combination with a threaded expander wedge constructed and arranged to be threaded on the threaded rod into the expansible gripping member in a wedging relationship.

An expansible gripping member has a distally extending formation arranged to deflect to lock the gripping member in position relative to the ring, preferably this formation comprising a set of circumferentially arranged, resilient fingers that are preferably integral with the main body of the gripping member.

An expansible gripping member has screw threads on its exterior that are disposed to engage and thread into ligament graft lying between the ring and the gripping member during advance of the gripping member.

The expansible gripping member supports a threaded rod extending proximally from the gripping member in combination with a threaded expander wedge threaded into the gripping member for a wedging relationship.

According to another aspect of the invention a device is provided for attaching a ligament graft to the inside of a bone tunnel from its proximal aspect (extra-articular point of access), the device comprising: a non-expansible structure ledge providing an interior passage through which the ligament graft may extend, the structure sized and adapted to fit within and be secured in the bone tunnel; a gripping member sized to be opposed to the ledge structure and to grip the ligament against a portion of the structure; and at least one strut extending distally from the portion of the ledge structure against which the ligament is gripped, a distal member disposed at the distal end of the strut in position to limit distal movement of the gripping member.

In preferred embodiments of this aspect of the invention the gripping member is expansible radially to grip the ligament against the ledge structure and position the ligament for incorporation by in-growth of bone from the wall of the tunnel. Preferably the ledge structure is carried on a continuous ring.

According to another aspect of the invention a device is provided for attaching a ligament graft to the inside of a bone tunnel from an extra-articular location, the device comprising: a rigid ring having an interior passage through which the ligament graft may extend, the ring sized and adapted to fit within and be secured in the bone tunnel; a gripping member constructed and arranged to grip a ligament graft against the interior surface of the rigid ring; and at least one strut extending proximally from the ring, a securing member attached to the proximal end of the strut, the securing member sized to engage an exterior surface of the bone to secure the ring in the cortical region of the bone tunnel.

Preferably the peripheral outer surface of the ring is cylindrical.

Preferred embodiments of this aspect of the invention have a bone-penetrating formation carried by the securing member.

Preferably the securing member is a flange extending laterally from the axis of the passage; preferably the flange has bone-penetrating formation, preferably projecting distally toward the bone.

In other embodiments the securing member is a flange having a hole sized to receive an awl-like tool to hold the member in position against rotation while a portion of the device is turned during the procedure.

Preferably, the gripping member is expansible to grip the ligament against the ring, and an expander is coupled to the expansible gripping member, constructed to expand the gripping member to grip the ligament against the ring.

Preferably the gripping member, when in position within the ring, has a distal portion extending beyond the ring that positions a corresponding portion of the ligament near or against the surface of the bone passage in the path of in-growing bone.

According to another aspect of the invention, a device is provided for attaching a ligament graft to the inside of a bone tunnel from its proximal aspect, the device comprising: a non-expansible ring having an interior passage through which the ligament graft may extend, the ring sized and adapted to fit within and be secured in the bone passage; strut portions extending proximally and distally from the ring; a securing member attached to the end of the proximally-extending strut portion, the securing member sized to engage an exterior surface of the bone to secure the ring in the cortical region of the bone tunnel; a base member attached to the distal end of the distally extending strut portion; a rod extending proximally from the base member through the ring; and a gripping member disposed between the rod and the ring, the gripping member constructed to grip the ligament against the ring.

Preferably the gripping member is expansible to grip the ligament against the ring.

According to another aspect of the invention a method is provided for attaching a ligament graft to the inside of a bone tunnel from a proximal location, the method comprising: providing a device according to any of the aspects of the invention, that have been described; providing a bone tunnel within a bone; introducing a non-expansible ring, or a rigid ring, with a ledge structure into the bone passage; passing the ligament graft through the interior passage of the introduced element; inserting a gripping member and expanding or otherwise urging the gripping member into a position that the gripping member grips the ligament against the introduced element, thereby securing the ligament graft to the inside of the bone tunnel. In preferred embodiments an expander is screwed into the gripping member or the radially expansible gripping member is screwed into the interior passage of the ring.

In the case of cruciate ligament graft, in which the graft is secured to the femur, the device is preferably introduced at an extra-articular location. Preferably multiple, e.g. 4, strands of graft, e.g. tendon, extend through the tunnel, preferably each of the grafts or at least pairs of grafts, being separated from the others in position for individual incorporation into in-growing bone.

BRIEF DESCRIPTION OF DRAWINGS OF PREFERRED EMBODIMENTS

FIG. 1A is a distal end view and

Figure 1:
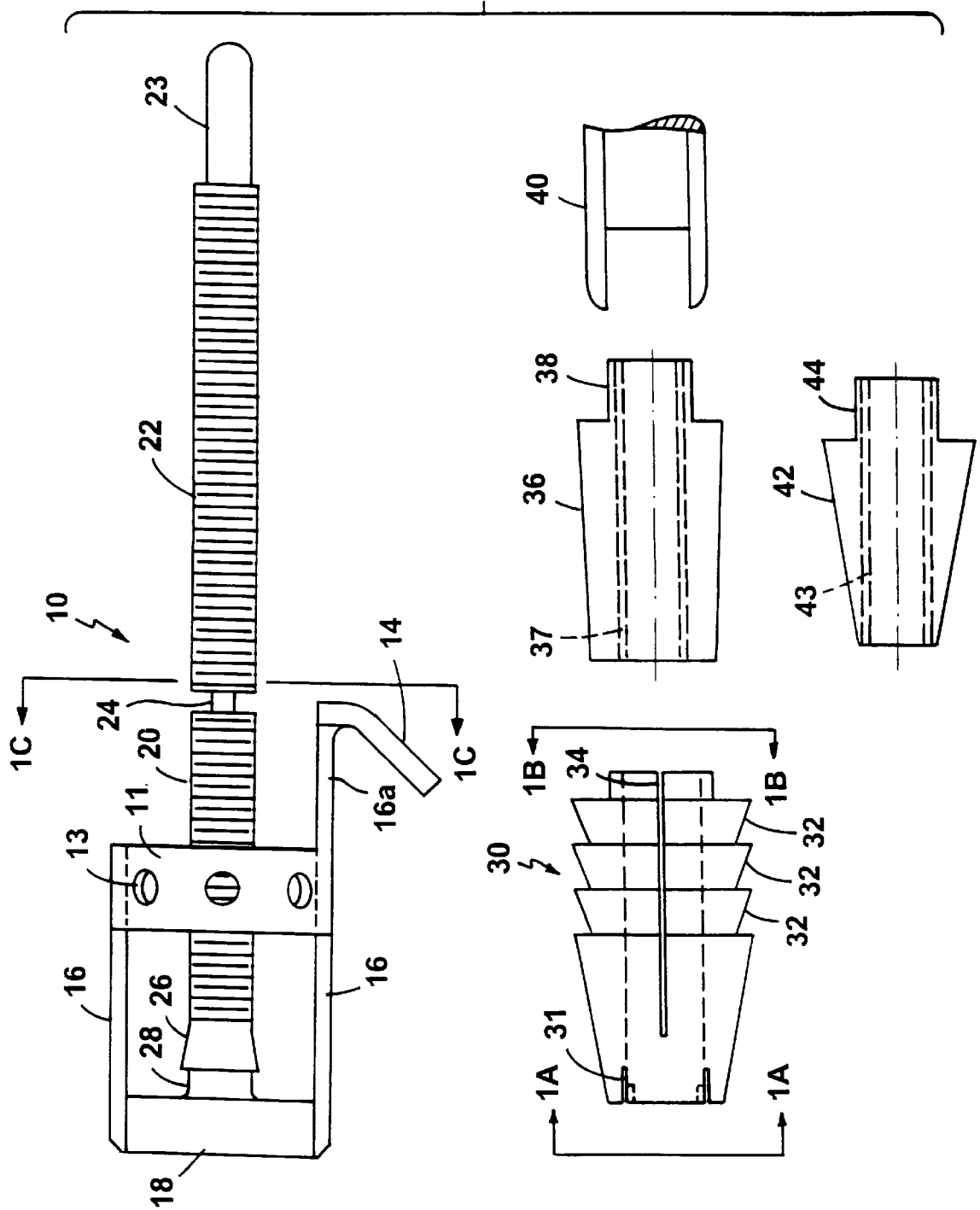
FIG. 1 is a side view of components that comprise a preferred ligament fixation set according to the invention.

FIG. 1B a proximal end view of an expandable gripping element component of the set taken respectively on lines 1A—1A and 1B—1B of FIG. 1.

FIG. 1C is a cross-sectional view taken on-line 1C—1C of FIG. 1, showing features of the fixed ring member.

FIG. 1D is a cross-section profile of the ring element of the fixed ring member taken on lines 1D—1D of FIG. 1C.

FIG. 2 is a view similar to FIG. 1 of another preferred fixed ring member while FIG. 2A is a partial side view of another preferred construction.

Figure 3A:
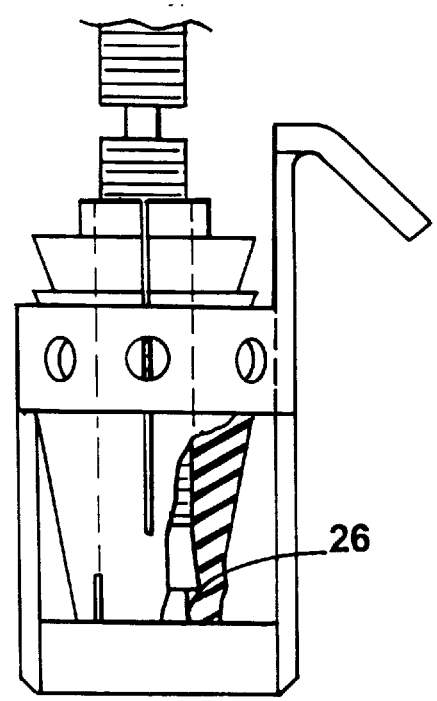
Figure 3:
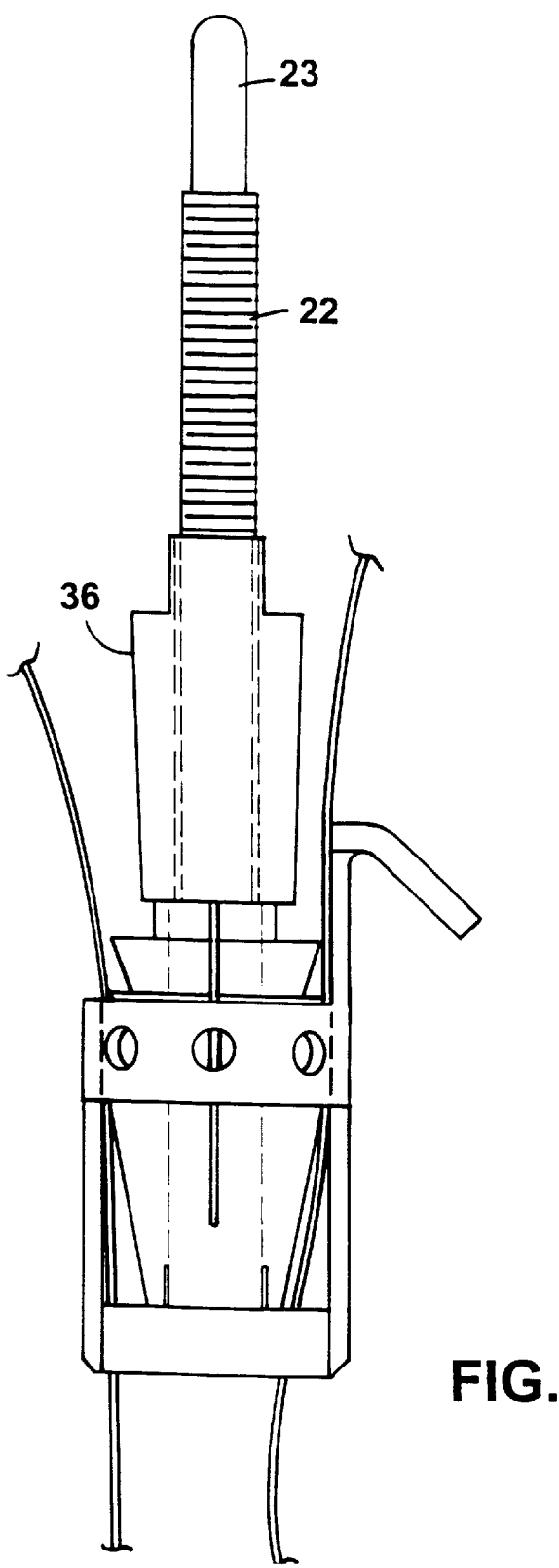

FIG. 3 is an assembly view, with ligament graft in place, showing the expandable gripping element seated in the fixed ring member by the driving component of the fixation set of FIG. 1.

FIG. 3A is a cut away view of part of the assembly of FIG. 3 showing details of the seating of the distal end of the gripping element.

FIG. 4 shows the expandable assembly of FIG. 3 with the gripping element now expanded by action of a conical wedge member of the set of FIG. 1.

Figure 5:
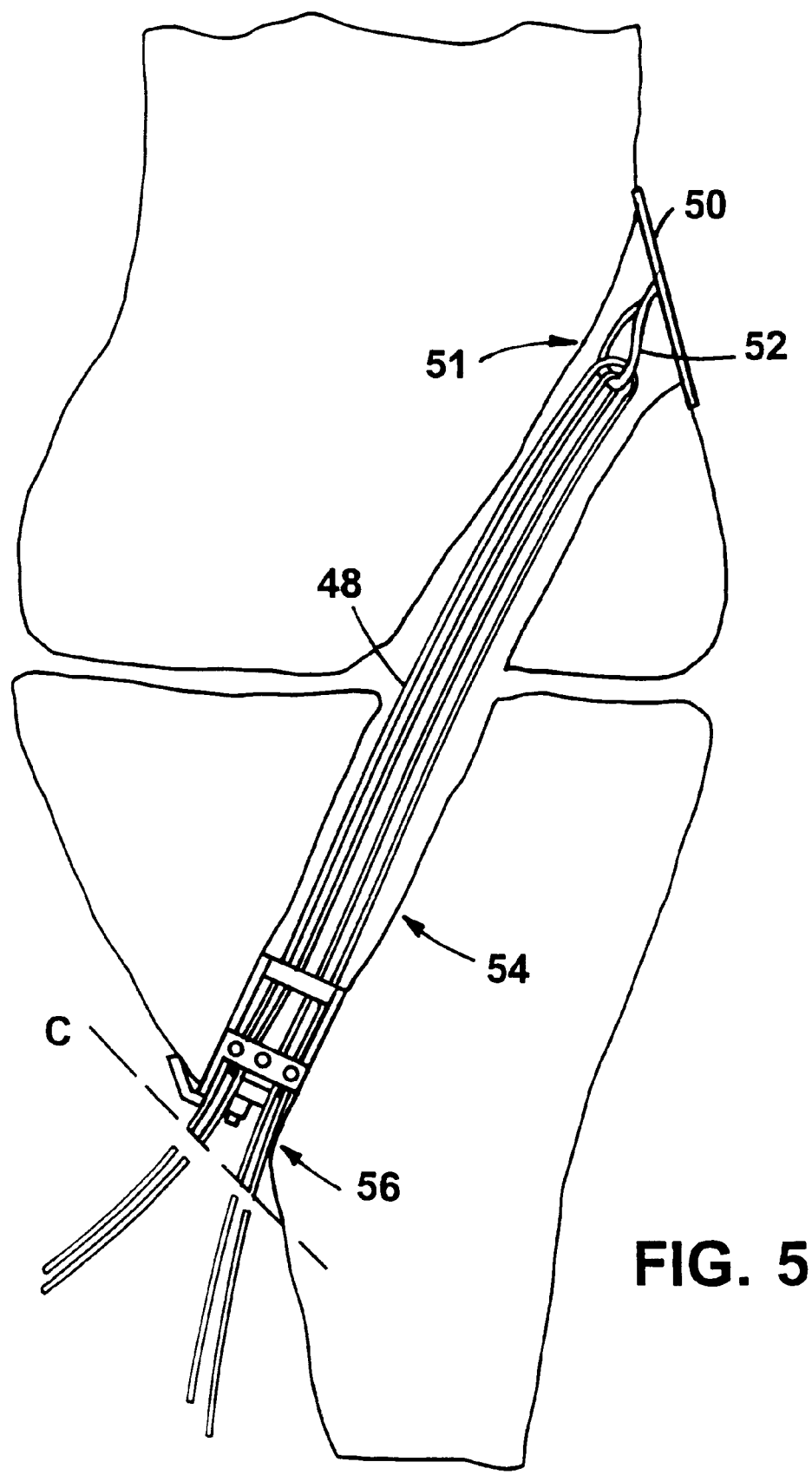

FIG. 4A is a diagrammatic view on an enlarged scale of the gripping action of the expanded gripping member against a preferred ledge formation of a fixed ring member FIG. 5 is a diagrammatic view of the ligament fixation device of FIG. 1 in place in a tibia tunnel, securing replacement ligaments in the knee.

Figure 6A:
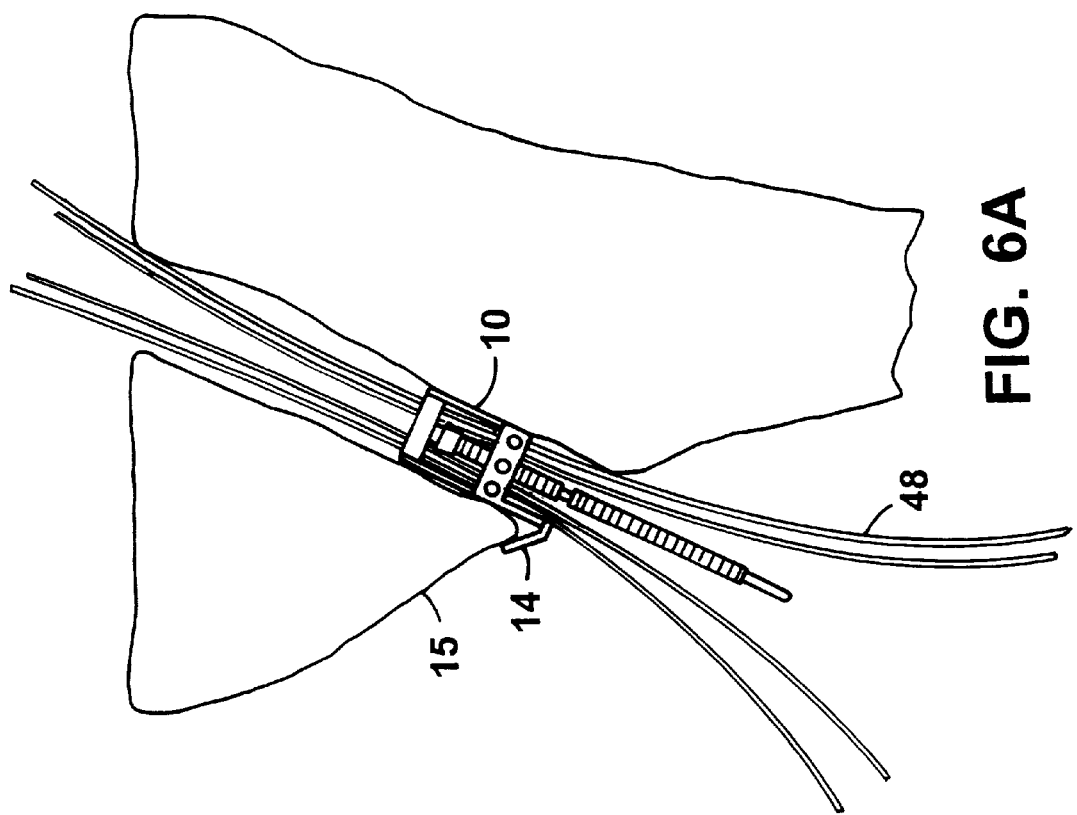
Figure 6:
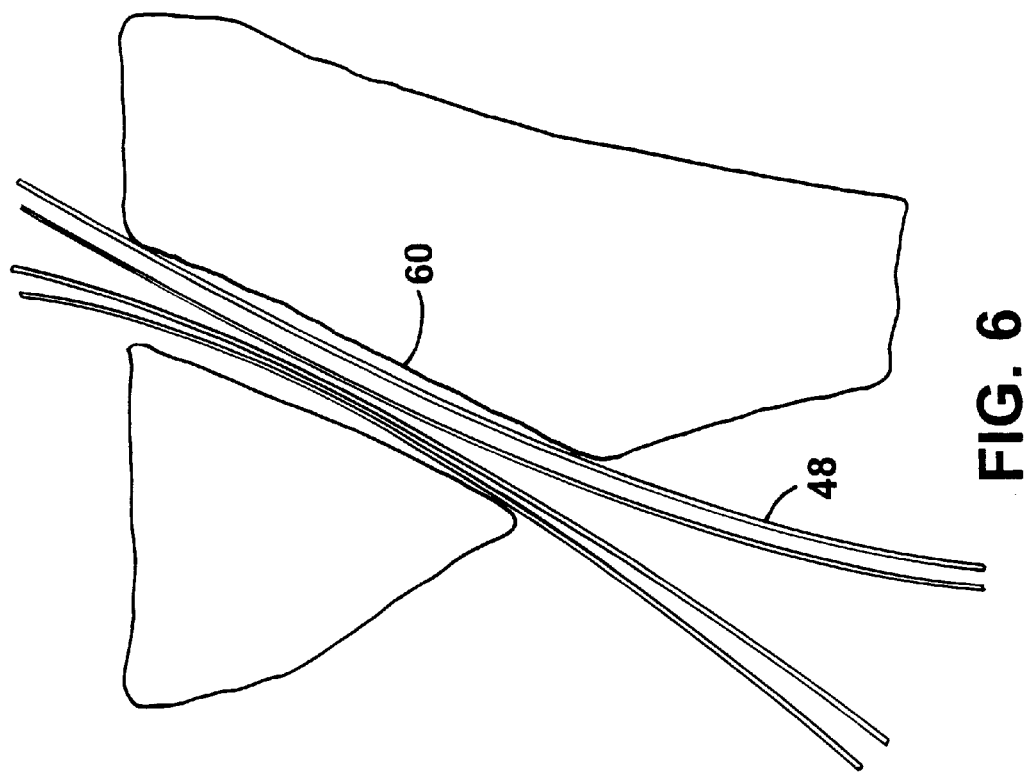
Figure 6C:
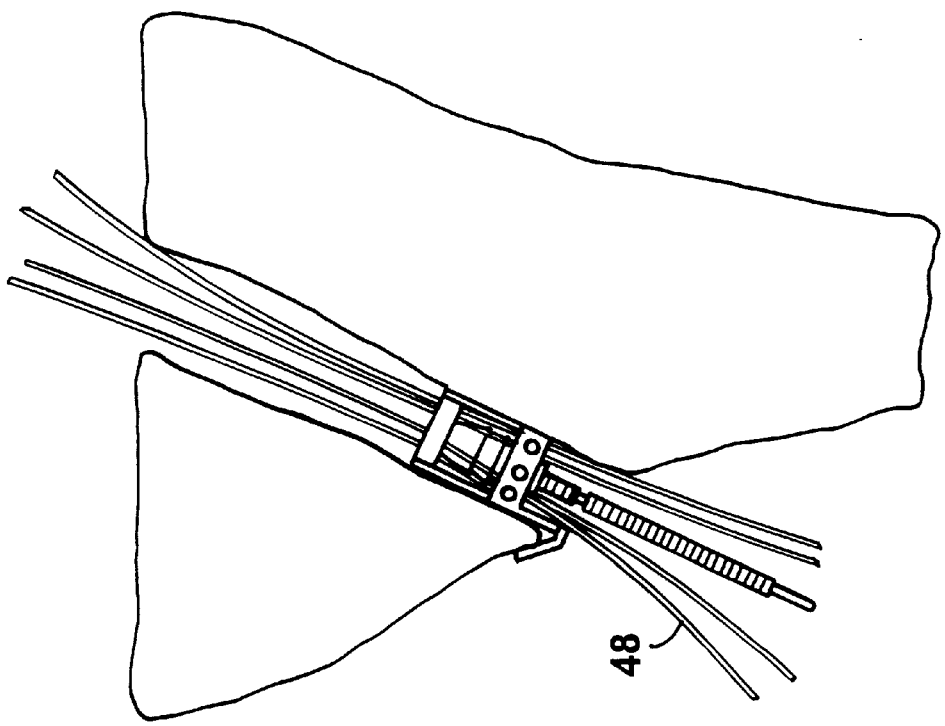
Figure 6B:
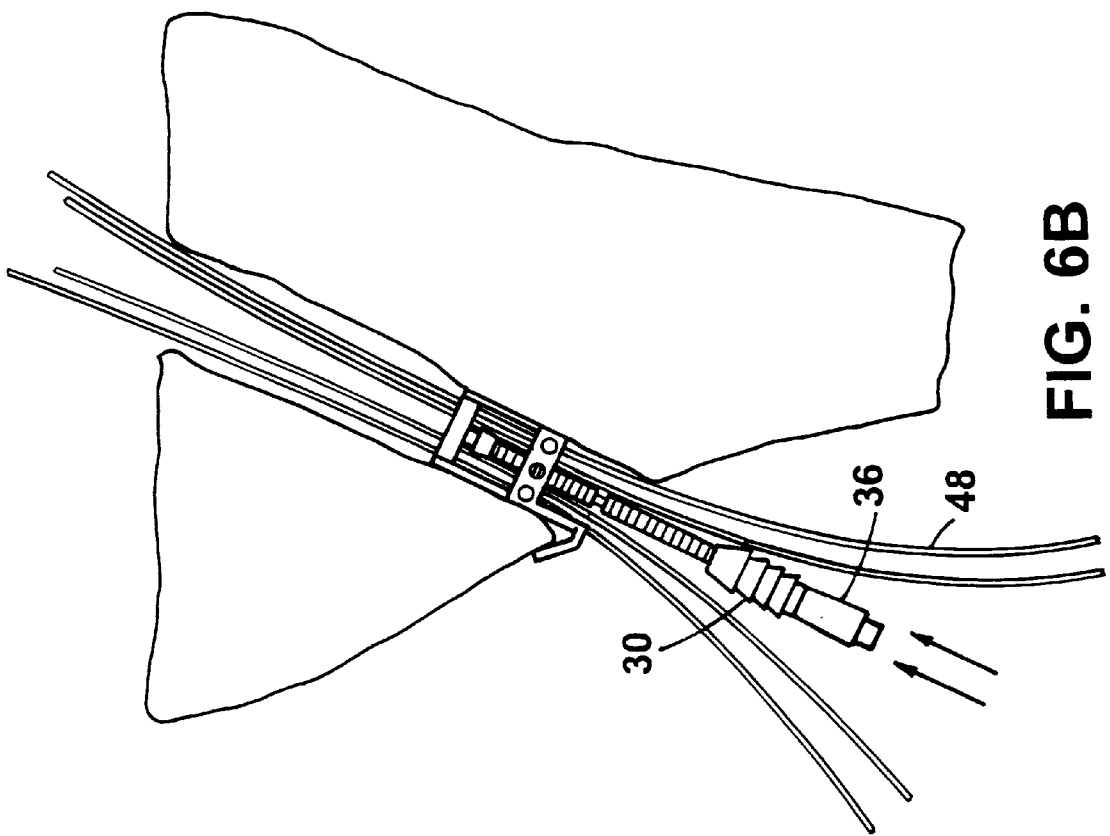
Figure 6E:
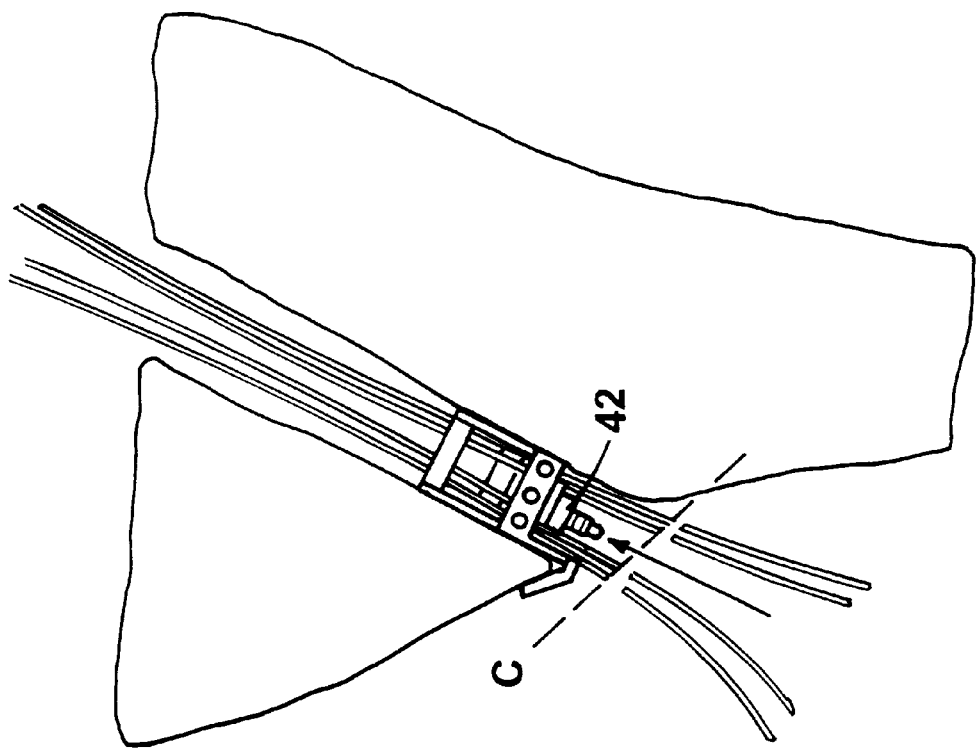

FIGS. 6 through 6E are views of the tibia of FIG. 5 illustrating the sequence of steps for placing the device in the tibia.

FIGS. 7A through 7C are views of another embodiment of the invention illustrating the sequence of steps for placing the device in the tibia.

FIG. 7D is an enlarged view showing a fixed ligament using the device shown in FIG. 7C.

Figure 8:
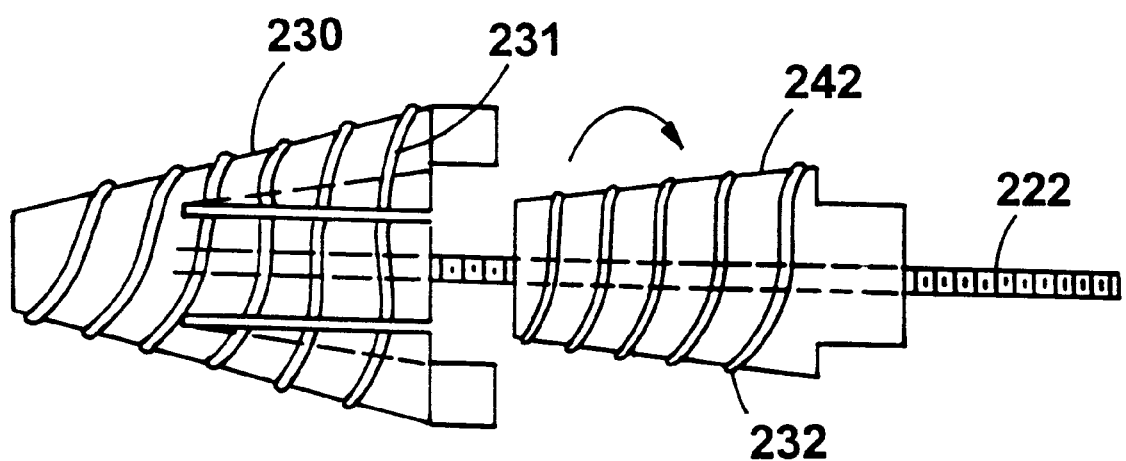

FIG. 8 is a view similar to parts of FIG. 7A of another embodiment of the invention.

DESCRIPTION OF PREFERRED EMBODIMENTS

FIG. 1 shows five parts that comprise a ligament fixation set. A fixed ring member 10 has ring element 11 that has on its inner periphery a fixed ledge 12 (See FIGS. 1C, 1D). The ring element 11, here in the form of a rigid cylindrical wall, has a series of in-growth apertures 13 formed in the wall. A pair of opposed distally extending struts 16 are integral with ring 11. Both extend distally to base 18. One of the struts has a proximally extending portion 16A which extends proximally to a retaining flange 14. The flange of Strut 16a serves as a buttress against the tibial cortex at the beginning of a tunnel in the tibia, the remainder of the device being sized to extend into the tunnel. Base 18 of ring member 10 supports a shaft that defines a threaded rod 20 that extends axially, parallel to struts 16 and proximally beyond ring element 11 to a joint 24 aligned with flange 14. A threaded rod extension 22 lying on the same axis is connected to threaded rod 20 by snap joint 24. At the proximal tip of the threaded rod extension is a reduced diameter pilot portion 23.

An expander formation 26 is formed as part of the shaft close to, but spaced proximally from base 18. The space between the expander and the base provides a relief region 28 defined by a reduced diameter portion at the root of the shaft.

The expandable gripping element 30 defines distal expansion sliding fingers 31 that are designed to resiliently spread and slide over the expander formation 26, and contract into the relief region 28, see FIG. 3A. The expandable gripping element 30 has angular gripping teeth 32 or ridges arranged to apply pressure to the ligament graft. The expandable gripping element 30 has proximal expansion slots 34 that allow expansion of distally extending, resilient portions of the expandable gripping element 30 by the conical wedge 42.

Also provided in the fixation set is driving nut 36 which has internal threads 37, matched to the external threads of the threaded rod 20, 22. The driving nut 36 has a driving head 38 for engagement by a hand powered driver 40 which is included in the fixation set. Only a portion of the driver is shown in FIG. 1. The remaining portion comprises a hollow shaft and handle such as that of a screw driver.

Also included in the set is conical wedge member 42. It has internal threads 43 also matched to the rod and a driving head 44 for engagement by driver 40.

An alternative construction of the ligament fixation device is shown in FIG. 2. In this case one of the struts 16 of the ring member has been eliminated. In the further embodiment of FIG. 2A, similar to that of FIG. 2, bone penetrating formations 46 depend from flange 14, for penetrating the tibia and locking the ring member from rotation.

In another embodiment a hole is provided in a flange for use of a awl-type instrument to securely hold the fixed ring member opposed to the tibia during the fixation procedure.

Use of the Ligament Fixation Device

Arthroscopic assisted ligament reconstruction of the knee requires rigid fixation of ligament grafts to bone. This enables accelerated rehabilitation and achievement of a stable knee. The present device enables secure fixation of soft tissue grafts, such as harvested tendons, to the endosteal surface of bone, that avoids reliance upon compression of the grafts against cancellous bone, and thus the strength of the fixation does not depend upon the underlying strength of the cancellous bone, and therefore promotes early rehabilitation even in the case of relatively soft cancellous bone.

In conjunction with the use of the ligament fixation device described, the grafts are secured on the femoral side of the knee using any of several methods. A common technique is to loop the tendons around a fixed post that is either attached to a button on the outer cortex of the femur or is placed directly across the femoral tunnel. Typically four strands of tendon are disposed across the knee joint for reconstructing the new ligament, which exit the joint through a tibial tunnel, to the outer cortex of the tibia.

Referring to FIG. 5, a ligament reconstruction technique is illustrated, that employs the device of the invention. Four ligament graft strands 48 extend from loops about a secure ring 52 which is attached to a button device 50 that is placed across the femoral tunnel 51. The four ligament grafts 48 traverse the tibial tunnel 54 and exit on the outer cortex of the tibia, 56.

FIG. 6 shows the four graft strands traversing the tibial tunnel 60 before the fixation device is in place. FIG. 6A illustrates introduction of the fixed ring member 10 in a fashion whereby two of the ligament grafts 48 pass on one side of the base 18 and two of the ligament grafts 48 pass on the other side. The ring member is inserted into the tibia tunnel 54 from the proximal aspect to the point where the retaining flange 14 is securely lodged upon the tibial cortex 15 as shown in FIG. 6A. If bone penetrating formations 46 as shown in FIG. 2a are employed, these penetrate the cortex and add to the action of the retainer flange 14 in securing the device to the tibial cortex. As shown in 6B, the expandable gripping element 30 is introduced into the ligament fixation ring member by sliding it over the pilot portion 23 of the threaded rod extension 22. The driving nut 36 is then also placed on the threaded rod extension 22, being introduced over pilot portion 23 of the rod. The driver 40 is then placed upon the driving head 38, and rotated clockwise to introduce the expandable gripping element into the fixation device to the point where the fingers defined by distal expansion slots 31 resiliently lock over the expander ledge 26, as shown in FIG. 3A. The driving nut 36 provides axial force to thus implant the expandable gripping element 30 in the device.

Figure 6D:
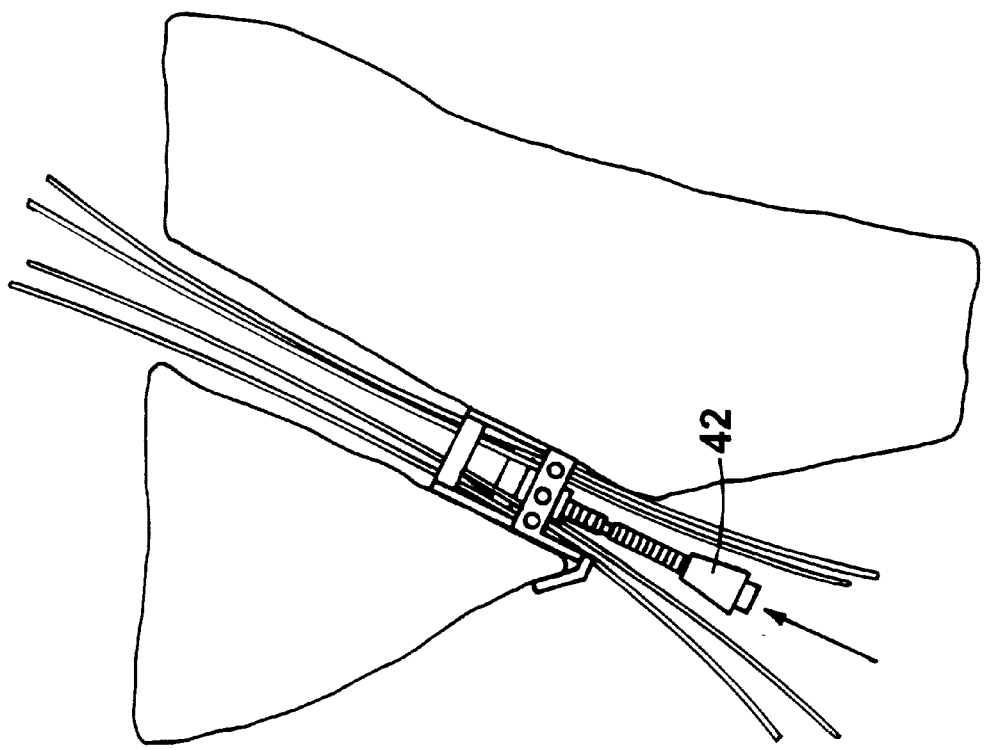

The driving nut 36 is then removed from the fixation device by rotating the driver 40 counterclockwise. As suggested in FIG. 6D, the conical wedge member 42 is then threaded on the threaded rod extension 22 over the pilot portion 23. The conical wedge is rotated past the snap joint 24 to the threaded rod region 20. It is driven into the expandable gripping element 30 by further rotation of the driver 40 until it is seated as is shown in FIG. 6E. As it is seated, the conical wedge surface 42 expands the proximal leg portions of the expandable gripping element 30, a motion permitted by the proximal expansion slots 34 formed in the member. The expanded condition obtained is shown in FIG. 4. Suitably high compression is developed between the expandable gripping element 30 and the interior surface of ring 11. The ligament grafts 48 which are separately disposed between ring 11 and expandable gripping element 30 are thus gripped securely by the expansion of expandable gripping element 30 toward the inner surface of ring 11. Where, as in the embodiment of FIG. 4A, an internal stress concentrating ledge 12 is provided on the ring, the maximum compression and securing action on the ligaments occurs in the vicinity of this ledge.

After suitable compression upon the ligament grafts has been achieved, the driver 40 is disengaged from the conical wedge and the threaded rod extension 22 is disengaged from the threaded rod 20 by bending applied to snap joint 24, that joint having been preselected to produce fracture under pressures that are not disruptive of the now-in place fixation device.

Recapping FIGS. 6–6C, FIG. 6 shows the four discrete ligament grafts traversing the tibial tunnel 60, FIG. 6a shows the introduction of the fixed ring member 10 with one pair of the ligament grafts 48 on one side and another pair of ligament grafts 48 on the other side of base 18, with the grafts exiting the tibial tunnel 54 through the fixed ring member 10. As shown in FIG. 6B, the expandable gripping element 30 is introduced by use of driving nut 36, the expandable gripping element 30 being driven into the fixed ring member 10 until the resilient elements forming its distal tip (enabled by distal expansion slots 31) have snapped over the expander ledge 26 as shown in FIG. 3A. The conical wedge 42 is introduced, FIG. 6D, to the point where the expandable gripping element 30 is compressed greatly against the inner aspect of the ring element 11, see FIGS. 4 and 4A.

As shown in FIG. 6E, the threaded rod extension 22 has been removed from the threaded rod 20 leaving the final fixation device configuration, i.e. the fixed ring member 10, securely implanted in the tibia with the expandable gripping element 30 compressed by the in-place conical wedge member 42. FIG. 4 shows the conical wedge member 42 expanding the expandable gripping element 30 within the fixed ring member 10. The ligament grafts 48 are cut off at the end of the procedure, shown as dotted line "C" in FIG. 6E.

Referring to the magnified view of FIG. 4A the ligament grafts 48 are shown wedged outwardly by the expandable gripping element 30. In the inner aspect of this embodiment of the ring element 11 there is a relatively narrow fixation ledge 12, at which the ligament grafts are tightly gripped with suitable non-damaging distortion of the grafts. The ligament grafts are transected at the end of the procedure just beyond the ring element 11. FIGS. 5 and 6E show by dotted line where the ligament grafts 48 are transected at the end of the procedure. The expandable portion of the distal aspect of the expandable gripping element provides an indication that the gripping element has been securely placed down to the base, which limits its motion and hence limits the available wedging movement to an appropriate amount. A mark on the driver or a mark on the flange may provide a visual verification that the gripping element has fully seated.

Operative Technicrue for Ligament Fixation Device

The arthroscopic assisted ACL reconstruction is performed with the leg either bent over the end of an operating room table or with the knee bent but with the patient supine on an operating table. Using hamstring tendons as the ligament graft requires the use of an incision on the proximal medial tibia of about 3 finger breadths length, placed just medial to the tibial tunnel. Through this incision the gracilis and semitendinosus tendons can be obtained as free grafts to reconstruct the anterior cruciate ligament.

A tunnel is drilled through this incision into the knee under arthroscopic visualization (all portions of the procedure that are to be performed intra-articularly are done under visualization by way of the arthroscope).

The tunnel which begins on the anteromedial tibia enters the intra-articular portion of the tibia at the insertion point of the anterior cruciate ligament on the tibia. Through this tibial tunnel a second tunnel is drilled into the femur. The second tunnel is placed at the second attachment site of the anterior cruciate ligament.

At this point there are two tunnels in the knee, one from the exterior portion of the tibia to the intra-articular region, and a second one in the femur, both tunnels as depicted in FIG. 5.

These tunnels are placed such that their openings are at the normal anterior cruciate origin and insertion sites.

At this point the grafts are placed across the knee, usually by use of sutures that are drilled through the lateral cortex of the femur and brought out to the lateral aspect of the thigh. The looped ends of the grafts are brought up into the femoral tunnel where they are secured by looping them around either a fixed post or the secure loop extending from a metal button as shown in FIG. 5. The grafts then lie across the knee joint in the anatomic configuration of the anterior cruciate ligament. They exit through the tibial tunnel and are splayed out through the incision on the proximal medial tibia.

These tendon grafts need to be securely fixed on the tibial side.

Many previous operative techniques have relied upon staples or screws and washers to secure tendon grafts to the tibial cortical surface. These fixation techniques leave painful, prominent hardware directly beneath the skin, their fixation strength is not always reliable, and a certain portion of tendon beneath these compressive devices is devascularized, that can be injurious.

The ligament fixation device here-described rigidly secures the ligament grafts within the tibial tunnel and leaves no prominent hardware. The construction enables in-growth of cancellous bone directly to the ligament grafts through apertures in ring element 11 and in the region just distal of ring element 11 where the tendons have been splayed out against or close to cancellous bone tissue.

The ligament fixation device thus provides temporary fixation until the body's normal healing process incorporates the ligament grafts into the bone. It is known from animal studies and clinical experience that by eight weeks, ligament grafts have incorporated into bone such that the weakest link of the new ligament construct is no longer the fixation point, but rather the intra-articular portion of the ligament. The presently preferred ligament fixation device provided herein has a relatively narrow ring element that minimizes the compression of the soft ligament tissue, the device providing a large open region distal to the ring element where the expandable gripping element pushes the ligament grafts into intimate contact with the cancellous bone to facilitate early healing of the grafts to the cancellous bone.

The rigid fixation of the hamstring grafts, thus achieved, can facilitate an accelerated rehabilitation, whereby a full range of motion and weight bearing, as tolerated, are begun based on patient comfort and not on any concern for protection of the fixation region.

An advantage of the ligament fixation device is that all of the ligament grafts are securely opposed to bone, allowing healing of each graft to bone so as to obtain the full strength potential of the composite.

Other Embodiments

In another embodiment, as shown in FIG. 7A, a fixed ring member 111 is implanted into a tibial tunnel 154, fixed ring member 111 being internally open, not having a threaded rod. A pair of opposed struts 116 are integral with ring 111 and support base 118 in position to limit distal advance of gripping element 130. Referring to FIG. 7A, the gripping element 130 has screw thread formations 132 on its conical exterior, constructed to be screwed into portions of graft 148 within ring member 111. Referring to FIG. 7B, the gripping element 130 is introduced to ring member 111 by rotation until its proximal end is roughly flush with ring member 111, at which point thread formations 132 interact with graft 148 to provide the reaction force that enables gripping element 130 to be driven into the tibial tunnel and into the inner portion of ring member 111. In so doing, the thread formations 132 of gripping element 130 deform the tendon (see FIG. 7D) and thereby define its path into ring member 111.

In a preferred modification shown in FIG. 8, a screw-form gripping member 230 has a hollowed bore 231 in its proximal portion and is expandable much in the nature of the expandable gripping element of FIG. 1. When seated, screw 230 is expanded securely toward ring member 111 by a second conical member 242 that is turned into bore 231 of the embodiment of FIG. 8 either by a threaded rod 222 incorporated into the plastic screw 230, extending proximally for receiving an expander 242 which may be identical to wedge member 42 of FIG. 1, or by the action of screw threads on the conical surface, that interact with the interior surface of the gripping element.

In a further alternative, the support base section may be omitted.

In preferred embodiments the ring member including its struts, base and flange are formed integrally of biologically acceptable, strong metal. The expansible gripping member advantageously is of one piece construction of engineering plastic that has suitable resiliency.

Numerous other embodiments employ other details to achieve secure fixation following the principles at various levels of generality, that have been presented here.

What is claimed is:

1. A device for attaching a ligament graft to the inside of a predetermined bone tunnel from its proximal aspect, the device comprising:
   a non-expansible ring having an interior passage through which the ligament graft may extend, the ring sized and adapted to fit within and be secured in the bone tunnel;
   a radially expansible gripping member sized to enter the ring and to press the ligament outwardly against the interior surface of the ring; and
   an expander coupled to the expansible gripping member, constructed to expand the expansible gripping member to grip the ligament against the ring, the device including a relatively narrow strut which extends from the ring proximally to a securing member attached to its proximal end, the securing member constructed and arranged to engage an exterior surface of the bone and to secure the ring in the cortical region of the bone passage at a position spaced distally from the exterior surface of the bone.

2. The device of claim 1 wherein the ring is rigid.

3. A device for attaching a ligament graft to the inside of a predetermined bone tunnel from its proximal aspect, the device comprising:
   a non-expansible ring having an interior passage through which the ligament graft may extend, the ring sized and adapted to fit within and be secured in the bone tunnel;
   a radially expansible gripping member sized to enter the ring and to press the ligament outwardly against the interior surface of the ring; and
   an expander coupled to the expansible gripping member constructed to expand the expansible gripping member to grip the ligament against the ring, and wherein the ring includes at least one aperture disposed to permit in-growth of bone about the ligament graft.

4. A device for attaching a ligament graft to the inside of a predetermined bone tunnel from its proximal aspect, the device comprising:
   a non-expansible ring having an interior passage through which the ligament graft may extend, the ring sized and adapted to fit within and be secured in the bone tunnel;
   a radially expansible gripping member sized to enter the ring and to press the ligament outwardly against the interior surface of the ring; and
   an expander coupled to the expansible gripping member, constructed to expand the expansible gripping member to grip the ligament against the ring, further comprising:
      at least one strut extending distally from the ring; and
      a distal member disposed at the distal end of the strut in position to limit distal movement of the gripping member.

5. The device of claim 4 in which there are at least two spaced apart struts that extend distally, in supporting relationship with said distal member.

6. The device of claim 4 in which the distal member is a base from which a rod extends proximally through the ring passage, upon which a member acts to expand the gripping member.

7. The device of claim 6 in which the rod is threaded and the gripping member is associated with a threaded expander engaged upon the threaded rod for expanding the expansible member.

8. The device of claim 7 in which the threaded expander is of wedge form, arranged to radially wedge apart portions of the expansible gripping member.

9. The device of claim 6, wherein a strut extends proximally from the ring to a securing member attached to its proximal end, the securing member constructed and arranged to engage an exterior surface of the bone and to secure the ring in the cortical region of the bone passage.

10. A device for attaching a ligament graft to the inside of a predetermined bone tunnel from its proximal aspect, the device comprising:
    a non-expansible ring having an interior passage through which the ligament graft may extend, the ring sized and adapted to fit within and be secured in the bone tunnel;
    a radially expansible gripping member sized to enter the ring and to press the ligament outwardly against the interior surface of the ring;
    an expander coupled to the expansible gripping member, constructed to expand the expansible gripping member to grip the ligament against the ring, the expansible gripping member comprising a set of circumferentially arranged proximally extending leg portions constructed and arranged to be splayed apart by wedging action of a centrally introduced member and in which the exterior surface of the leg portions have ligament gripping projections, and in which the ring supports a threaded rod that extends through the gripping member, in combination with a threaded expander wedge constructed and arranged to be threaded on the threaded rod into the expansible gripping member in a wedging relationship.

11. A device for attaching a ligament graft to the inside of a predetermined bone tunnel from its proximal aspect, the device comprising:
    a non-expansible ring having an interior passage through which the ligament graft may extend, the ring sized and adapted to fit within and be secured in the bone tunnel;
    a radially expansible gripping member sized to enter the ring and to press the ligament outwardly against the interior surface of the ring;
    an expander coupled to the expansible gripping member, constructed to expand the expansible gripping member to grip the ligament against the ring, the expansible gripping member comprising a set of circumferentially arranged proximally extending leg portions constructed and arranged to be splayed apart by wedging action of a centrally introduced member and in which the exterior surface of the leg portions have ligament gripping projections, and in which the expansible gripping member supports a threaded rod extending proximally from the gripping member in combination with a threaded expander wedge constructed and arranged to be threaded on the threaded rod into the expansible gripping member in a wedging relationship.

12. A device for attaching a ligament graft to the inside of a predetermined bone tunnel from its proximal aspect, the device comprising:
    a non-expansible ring having an interior passage through which the ligament graft may extend, the ring sized and adapted to fit within and be secured in the bone tunnel;
    a radially expansible gripping member sized to enter the ring and to press the ligament outwardly against the interior surface of the ring;
    an expander coupled to the expansible gripping member, constructed to expand the expansible gripping member to grip the ligament against the ring, and in which the expansible member supports a threaded rod extending proximally from the gripping member in combination with a threaded wedge element constructed and arranged to be threaded on the threaded rod into the expansible gripping member in a wedging relationship.

13. The device of claim 12 in which the securing member is a flange having bone-penetrating formations.

14. A device for attaching a ligament graft to the inside of a bone tunnel from a proximal aspect, the device comprising:
- a non-expansible ledge structure providing an interior passage through which the ligament graft may extend, the structure sized and adapted to fit within and be secured in the bone tunnel;
- a gripping member sized to be opposed to the ledge structure and to grip the ligament against a portion of the ledge structure; and
- at least one strut extending distally from the portion of the ledge structure against which the ligament is gripped,
- a distal member disposed at the distal end of the strut in position to limit distal movement of the gripping member.

15. The device of claim 14 in which the gripping member is expansible radially to grip the ligament against the ledge structure and position the ligament for incorporation by in-growth of bone from the wall of the tunnel.

16. The device of claim 14 in which the ledge structure is carried on a continuous ring.

17. A device for attaching a ligament graft to the inside of a bone tunnel from an extra-articular location, the device comprising:
- a rigid ring having an interior passage through which the ligament graft may extend, the ring sized to fit within the bone tunnel;
- a gripping member constructed and arranged to grip a ligament graft against the interior surface of the rigid ring; and
- at least one relatively narrow strut extending proximally from the ring,
- a securing member attached to the proximal end of the strut, the securing member sized to engage an exterior surface of the bone to secure the ring in the cortical region of the bone tunnel at a position spaced distally from the exterior surface of the bone.

18. The device of claim 17 in which the peripheral outer surface of the ring is cylindrical.

19. The device of claim 17 in which the securing member is a flange.

20. The device of claim 17 in which the gripping member is expansible to grip the ligament against the ring; and
- an expander is coupled to the expandable gripping member, constructed to expand the gripping member to grip the ligament against the ring.

21. The device of claim 20 in which the gripping member, when in position within the ring, has a distal portion extending beyond the ring that positions a corresponding portion of the ligament near or at the surface of the bone passage in the path of in-growing bone.

22. The device of claim 17 in which the gripping member is expansible to grip the ligament against the ring.

23. A device for attaching a ligament graft to the inside of a bone tunnel from an extra-articular location, the device comprising:
- a rigid ring having an interior passage through which the ligament graft may extend, the ring sized to fit within the bone tunnel;
- a gripping member constructed and arranged to grip a ligament graft against the interior surface of the rigid ring;
- at least one strut extending proximally from the ring,
- a securing member attached to the proximal end of the strut, the securing member sized to engage an exterior surface of the bone to secure the ring in the cortical region of the bone tunnel, and in which a bone-penetrating formation is carried by the securing member.

24. A device for attaching a ligament graft to the inside of a bone tunnel from an extra-articular location, the device comprising:
- a rigid ring having an interior passage through which the ligament graft may extend, the ring sized to fit within the bone tunnel;
- a gripping member constructed and arranged to grip a ligament graft against the interior surface of the rigid ring;
- at least one strut extending proximally from the ring,
- a securing member attached to the proximal end of the strut, the securing member sized to engage an exterior surface of the bone to secure the ring in the cortical region of the bone tunnel, and in which the securing member is a flange having a hole sized to receive an awl-like tool to hold the member in position against rotation while a portion of the device is turned during the procedure.

25. A device for attaching a ligament graft to the inside of a bone tunnel from a proximal aspect, the device comprising:
- a non-expansible ring having an interior passage through which the ligament graft may extend, the ring sized and adapted to fit within and be secured in the bone passage;
- strut portions extending proximally and distally from the ring;
- a securing member attached to the end of the proximally-extending strut portion, the securing member sized to engage an exterior surface of the bone to secure the ring in the cortical region of the bone tunnel;
- a base member attached to the distal end of the distally extending strut portion;
- a threaded rod extending proximally from the base member through the ring;
- and a gripping member disposed between the rod and the ring, the gripping member constructed to grip the ligament against the ring.

* * * * *